United States Patent [19]
Cassani et al.

[11] Patent Number: 5,656,491
[45] Date of Patent: Aug. 12, 1997

[54] MOBILE-MODULE PLANT FOR THE DEVELOPMENT AND THE PRODUCTION OF BIOTECHNOLOGICAL PRODUCTS ON A PILOT SCALE

[75] Inventors: Giovanni Rodolfo Cassani, Pavia; Marina Barbara Lani, Lesmo, both of Italy

[73] Assignees: Snamprogettibiotecnologie S.p.A., Vibo Valentia; Tecnogen S.c.P.A., Piana di Monte Verna, both of Italy

[21] Appl. No.: 343,542

[22] PCT Filed: May 29, 1993

[86] PCT No.: PCT/EP93/01401

§ 371 Date: Nov. 29, 1994

§ 102(e) Date: Nov. 29, 1994

[87] PCT Pub. No.: WO93/25657

PCT Pub. Date: Dec. 23, 1993

[30] Foreign Application Priority Data

Jun. 9, 1992 [IT] Italy ................... MI92A1417

[51] Int. Cl.⁶ .............. A01N 1/02; G01N 33/50; E04H 1/00
[52] U.S. Cl. ................... 435/283.1; 435/287.1; 435/289.1; 435/308.1; 422/50; 422/99; 422/129; 422/187; 52/79.1; 52/143
[58] Field of Search ............. 435/283.1, 290.1, 435/287.1, 289.1, 308.1; 422/50, 99, 104, 129, 187; 52/27, 79.1, 143, 174; 57/79.7, 79.8

[56] References Cited

U.S. PATENT DOCUMENTS 4,850,268  7/1989  Saito et al. ............... 98/33.1
5,195,922  3/1993  Genco ....................... 454/57
5,259,812  11/1993  Kleinsek .................... 454/57
5,366,896  11/1994  Margrey et al. .............. 436/48

FOREIGN PATENT DOCUMENTS 2 605 901  3/1988  France ................ B01L 1/00
3426717A1  1/1986  Germany ............... C02F 11/04
2 152 878  1/1985  United Kingdom ....... B25J 2/02

OTHER PUBLICATIONS

Analytical Chemistry, vol. 63, No. 11, 1 Jun. 1991, Columbus US pp. 641–642 644, A.R. Newman 'Portable Analytical Instruments' see p. 644.

DD, C, 82 510 (Karl–Friedrich Poulheim) 12 Jun. 1971, see p. 2, paragraph 2–p. 3, paragraph 2; claim 1.

*Primary Examiner*—David A. Redding
*Attorney, Agent, or Firm*—Nixon & Vanderhye, P.C.

[57] ABSTRACT

A mobile-module plant (1) for the development and the production of biotechnological products on a pilot scale comprising equipments for the production, separation, purification and finishing of said products (11, 17, 18, 19, 20; 40, 47, 48, 50, 52, 54; 71–76, 82, 86, 89, 92, 95, 98) and auxiliary equipments (102; 107, 109, 110; 112; 113; 119; 123; 129; 134; 135; 141–143), wherein (i) the plant (1) consists of at least two mobile modules (2; 3; 4; 5; 8) suitable for being connected together and integrated one with the other. Each of the mobile modules (2; 3; 4; 5; 8) comprises a movable container (6). At least one of the movable containers (6) is provided with a preselected own set of said equipments (11, 17, 18, 19, 20; 40, 47, 48, 50, 52, 54; 71–76, 82, 86, 89, 92, 95, 98; 102; 107, 109, 110; 112; 113; 119; 123; 129; 134; 135; 141–143). At least one of the movable containers (6) is aseptic.

12 Claims, 6 Drawing Sheets

MOBILE-MODULE PLANT FOR THE DEVELOPMENT AND THE PRODUCTION OF BIOTECHNOLOGICAL PRODUCTS ON A PILOT SCALE

BACKGROUND

1. Field of the Invention

The present invention relates to a mobile-module plant for the development and the production of biotechnological products on a pilot scale comprising equipments for the production, separation, purification and finishing of said products.

2. Related Art and other Considerations

Firms of a biotechnologicaL character carry out essentially two types of activity: applied research and production.

Passage from one activity to the other implies the development of the production method on a pilot scale. Usually, the pilot plant is then also used for commercial production, at least until the quantity of the product required by the market does not impose the construction of a plant on a larger scale.

The development step on a pilot scale causes different types of problems to the entrepreneur facing them, first of all the financial resources.

Firms having sufficient financial means generally build a plant specific for the product under development. But this solution is not exempt from drawbacks; indeed, investments, in addition to being difficult to estimate, imply the purchase and installation of equipments that cannot usually be reused. Thus, when development has a negative result, the investment is a total loss. In addition, during development, the need can arise of having to use apparatus that are different from those already installed so that, even in this case, efforts and investments already made are brought to nought if the necessary changes cannot be made due to a lack of time or space. The time required to build a specific plant is fairly long, generally of the order of two years, and this causes a corresponding delay in the start of production, with a substantial increase in the project's financial risk. In fact, delays of this magnitude are well-known to be very dangerous in sectors subject to highly rapid technological development such as is the current case with biotechnoloy, because they may make obsolete the product and the development process, even during the plant's construction phase.

In turn, firms having insufficient financial resources find themselves in the position of having to entrust the development to firms specialized in third-party manufacturing, thus divulging their know-how and laying the foundations for possible conflicts in relation to the paternity of possible inventive contributions during the course of development.

SUMMARY

The object of the present invention is to solve the abovementioned problems by means of a system of mobile, movable modules that can be connected together and integrated one with the other and capable of forming, in a very short time, a plant for the development and production of biotechnological products on a pilot scale, having the desired characteristics. The plant can be disassembled just as quickly into the individual modules, which may be moved easily to other locations to be subsequently connected together and integrated one with the other or with other modules, so as to form another plant having features that may even be different from those of the first plant.

The object of the present invention is thus a mobile-module plant for the development and production of biotechnological products on a pilot scale comprising equipments for the production, separation, purification and finishing of said products and auxiliary equipments, characterized in that (i) the plant is comprised of at least two mobile modules suitable for being connected together and integrated one with the other, (ii) each of the mobile modules comprises a movable container, (iii) at least one of the movable containers is provided with a preselected own set of the equipments, and (iv) at least one of the movable containers constitutes an aseptic environment.

During the course of the present description and of the following claims, the term "aseptic" used in relation to a module or a container indicates that the environment of the module or container is provided with an air conditioning system such as to ensure values of temperature, relative humidity, and particle content within preset limits. The same term "aseptic" used in relation to a piece of equipment indicates that such equipment can be easily sterilized with conventional techniques.

According to the equipments that they contain and to their function, the mobile modules according to the present invention may be divided into real production modules and into auxiliary modules.

Typically, the production modules according to the present invention contain tanks for nutrient means, tanks for acid, basic and buffer solutions, bioreactors or other equipments for the culture of micro-organisms or other biological entities possibly modified, such as genetically engineered, centrifuges, ultra-filtration and homogeneization equipments, chromatography columns, vacuum freeze driers, autoclaves or other equipments commonly used in biotechnological processes.

The abovementioned production modules are aseptic.

In turn, the auxiliary modules can contain equipments such as air conditioners, generator sets, cooling water production units, clean steam and industrial steam boilers, water softeners, reverse osmosis units, stills, heat exchangers, hot water production systems, air compressors, and such like. These modules may or may not be aseptic according to the equipments they contain.

A further auxiliary module, typical of the present invention, is an aseptic connecting module, accessible by the operators, that may be sealingly connected between the outer environment and at least one production module or that may be interposed between two production modules or between one production module and an auxiliary one.

Preferably, the mobile modules constituting the plant according to the present invention, are mounted each on a trailer suitable for being connected to a tractor or on a railway car.

To advantage, equipments for the culture, separation, purification and finishing are grouped together in three distinct production modules but they may also be grouped together in a different manner.

All or part of the equipments which it is preferred to group together in the service modules may also, in special cases, be housed in one or more production modules.

The plant according to the present invention comprises, preferably, an auxiliary module and at least one aseptic production module connected together and with the outer environment by means of a sealed aseptic connecting module.

According to a possible realization the plant, according to the present invention, comprises an auxiliary module, a fermentation or culture module, a separation module and a purification and finishing module, and said modules are connected together and integrated one with another through sealed aseptic connecting modules.

The plant according to the present invention ensures maximum flexibility, because it allows the user to equip himself with the type and the number of modules necessary to meet his needs.

BRIEF DESCRIPTION OF THE DRAWINGS

Features and advantages of the invention shall now be illustrated with reference to a realization of the invention represented as non-limiting example in the enclosed figures, wherein:

In FIG. 1 there is indicated as a whole with 1 a plant for the development and production of biotechnological products on a pilot scale, made according to the invention, wherein useful chemical compounds are prepared, say, for diagnostic and therapeutic use, by means of microorganisms or animal or vegetable biological entities, say, bacteria or animal or vegetable cells or yeasts, possibly genetically modified.

DETAILED DESCRIPTION OF THE DRAWINGS

Figure 1:
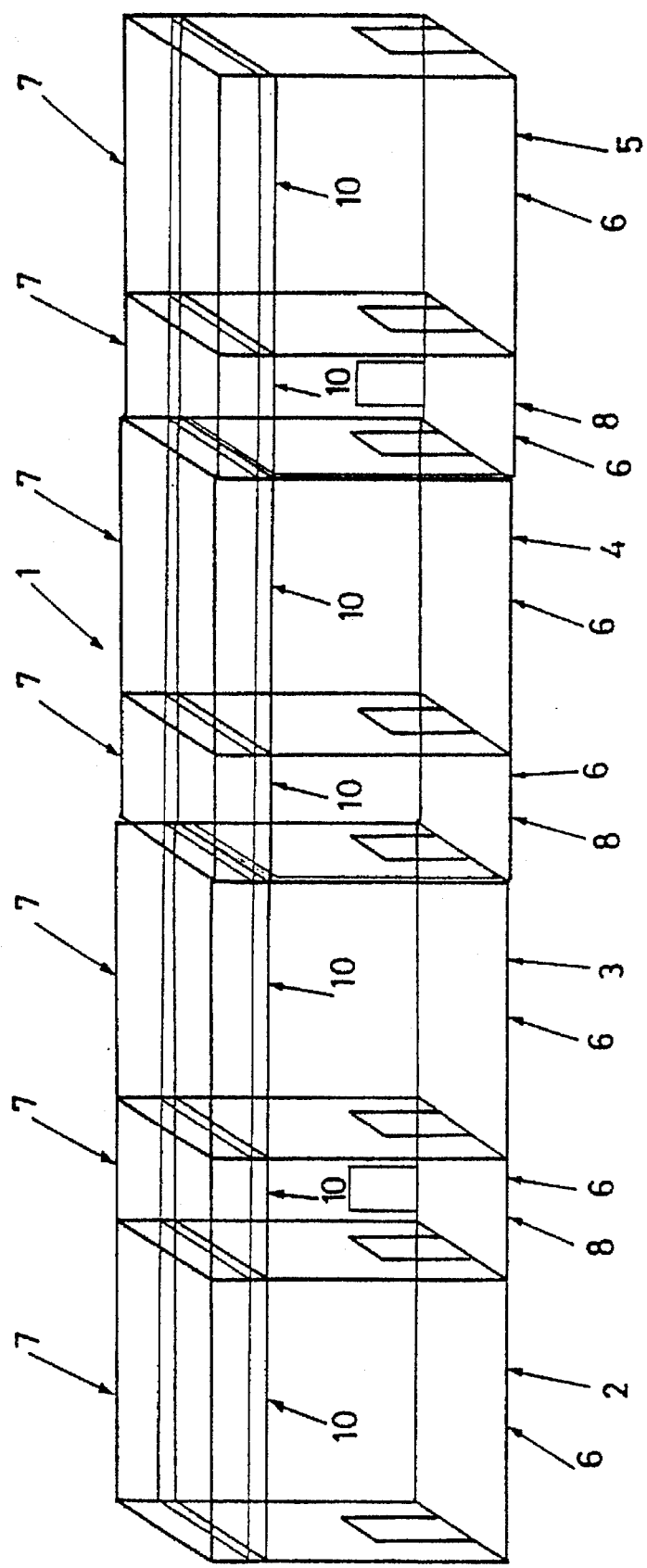
FIG. 1 shows diagramatically a plant for the development and production of biotechnological products on a pilot scale according to the present invention.

The plant 1 comprises an auxiliary module 2 and aseptic production modules comprised of a culture module 3, a separation module 4 and a purification and finishing module 5. Each module 2, 3, 4, 5 is enclosed in a corresponding container 6. In the case of modules 2, 3, 4 and 5 the container 6 is thermally insulated; in the case of modules 3, 4 and 5 the container 6 is also aseptic, and forms a clean room, that is to say, a room whose floor, walls and ceiling are built and finished with materials conventionally suitable for not releasing any contaminant inside the room, of adequate thickness and type of finish, easy to be sterilized and cleaned with products that are not toxic to human beings. The ceiling of each aseptic container 6 is provided with a corresponding space 10 for the passage of pipes, not shown, for fluids, such as demineralized water, water for injection, cooled water, clean and industrial steam, from the auxiliary module 2. Floor, walls and ceiling are provided with ports, also not shown, for the passage of air provided by an air conditioning system, also not shown, as it is known, housed in a respective space 7 of the ceiling. The air conditioning system, that may also be housed in a space on the side of the corresponding container 6, has the task of treating the incoming and outgoing air so as to keep the values of temperature, relative humidity, and particle content within pre-set limits, and to avoid any possible contamination deriving from any polluting source, so as to protect staff, the products and the external and internal environment.

Modules 2 and 3 are connected together by a sealed and aseptic connecting module, indicated as a whole with 8, that can be assembled and dis-assembled according to needs. Modules 3 and 4 and modules 4 and 5 are also connected together by respective aseptic and sealed connecting modules 8.

Each aseptic connecting module 8 forms a passage for the entry and exit of staff from the production modules 3, 4, 5; to advantage, it comprises dressing rooms, not shown, and a space for the passage of materials. Each passage module 8 is enclosed within a corresponding container 6, aseptic and thermally insulated, suitable for forming a clean room, similar to those of modules 3, 4, 5. The ceiling of container 6 is provided with a respective technical space 10 for the passage of fluid pipes from the service module 2 and leading to the production modules. In addition, each connecting module 8 is provided with a respective air conditioning system, arranged in a space of its own 7 of the ceiling.

The plant 1 is thermally insulated, has a self-contained air conditioning system and is especially suitable for being installed outdoors. Thus, since it does not need any fixed infrastructure, it can be installed very quickly with no additional costs.

Figure 2:
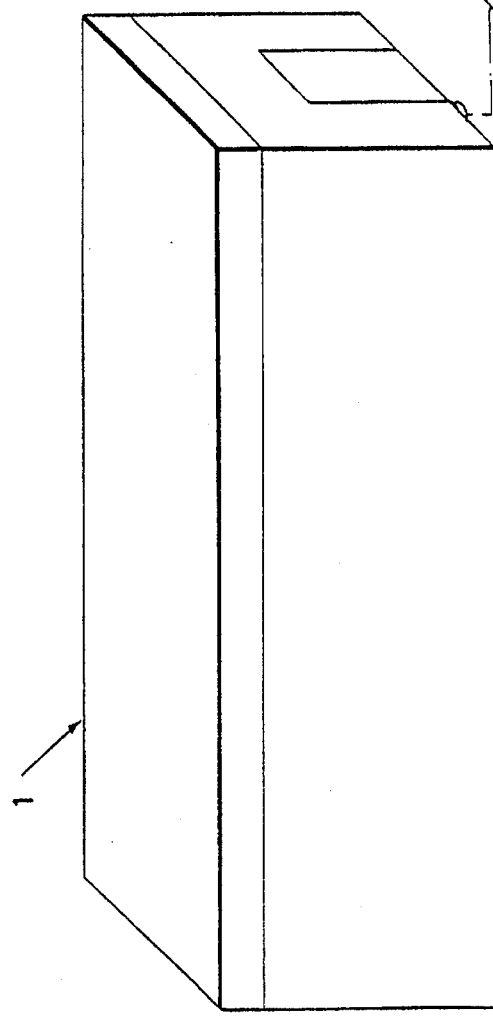
FIG. 2 shows the plant of FIG. 1 in a mobile realization.
Figure 2:
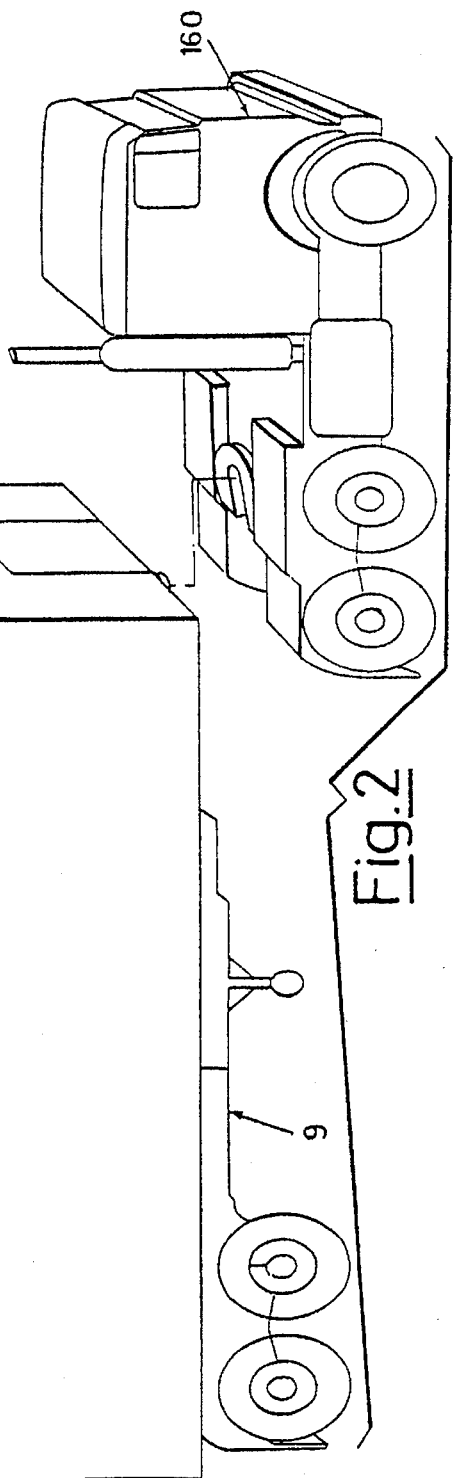

The plant 1, assembled as shown in FIG. 1, is constituted by mobile modules whose containers have the following dimensions: width ranging from 2.5 to 3 m; length ranging from 7 to 12 m; height ranging from 3 to 3.6 m. The modules constituting the plant 1 are mobile and each of them may be mounted on a trailer 9 of a trailer to be moved by means of a tractor 160, as shown in FIG. 2, or it can be loaded and moved on a railway car.

Figure 3:
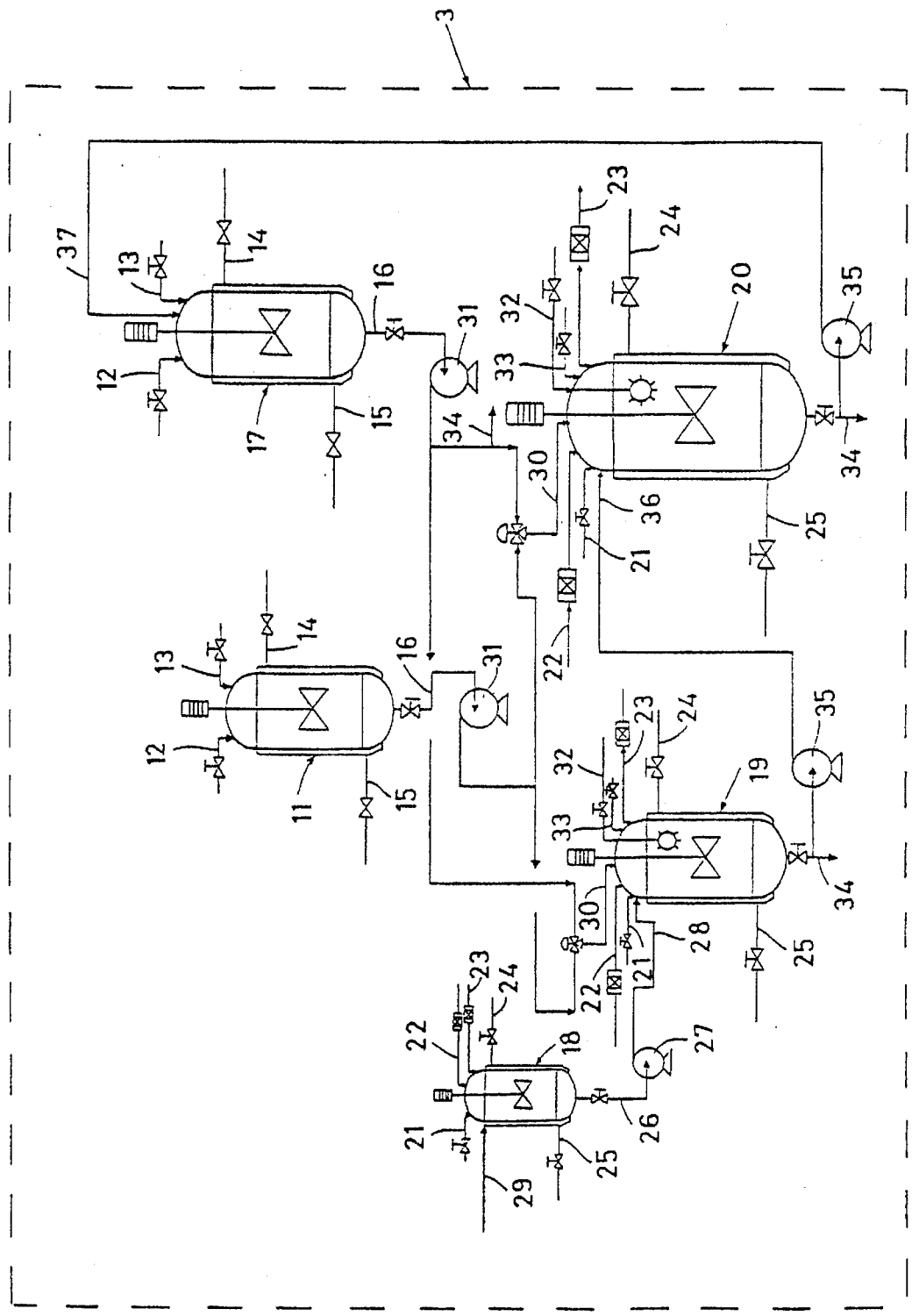
FIG. 3 shows schematically a culture production module of the plant of FIG. 1.

As shown in FIG. 3, the culture module 3 comprises a pair of tanks, for the formation of a first and of a second nutrient, indicated as a whole with 11 and 17, provided with a stirrer and a fluid circulation jacket. To each tank 11 and 17 there are connected a respective inlet conduit 12 of a nutrient in powder or liquid form, a respective inlet conduit 13 of water for injection, respective inlet and outlet conduits 14 and 15 of a cooling liquid or steam from its jacket, a respective outlet conduit 16 of a nutrient that may be used as a culture medium by fermentation.

The culture module 3 also comprises three bioreactors, indicated as a whole with 18, 19, 20, preferably having a capacity of 2, 20 and 200 l, respectively. Each of said bioreactors is provided with a stirrer and fluid circulation jacket, possibly removable, or replaceable with another model.

The technician of the art shall understand that this arrangement of the bioreactors is specific for the process illustrated below, while other processes may require different typologies, dimensions, arrangements and a different number of bioreactors.

To the bioreactor 18 there are connected an inlet conduit 29 for inoculum, an inlet conduit 21 for acid or base, conduits 22 and 23, provided with filters, of air inlet and outlet, respectively, conduits 24 and 25 for supplying cooling liquid or steam to its jacket and an output conduit 26 for the fermented broth that, through a peristaltic pump 27, is connected to an inlet conduit 28 in the bioreactor 19.

To each bioreactor 19 and 20 there are connected a respective inlet conduit 30 for nutrient, supplied by conduits 16 by means of respective peristaltic pumps 31, respective inlet conduits 21, 32 and 33 for acid or base, for defoam agent and for a washing solution, respectively, respective inlet and outlet conduits 22 and 23 for air, respective inlet and outlet conduits 24 and 25 for cooling liquid or steam from its jacket, and a respective outlet conduit 34 of fermented broth.

The outlet conduit 34 from the bioreactor 19 is also connected, through a peristaltic pump 35, to the inlet conduit 36 in the bioreactor 20, while the outlet conduit 34 from the bioreactor 20 is also connected, through a peristaltic pump 35, to an inlet conduit 37 in the tank 17 for the production of the second nutrient.

Figure 4:
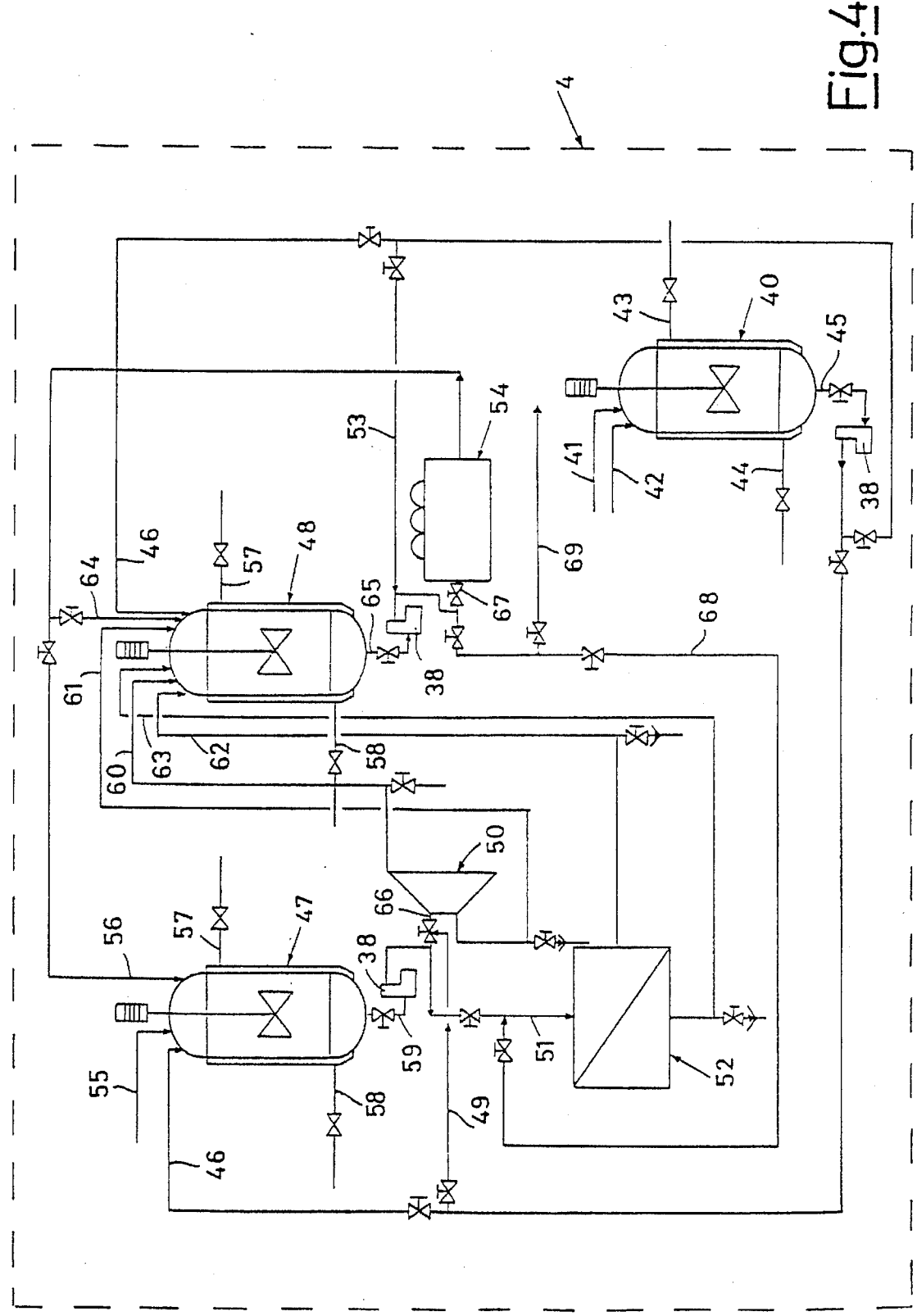
FIG. 4 shows schematically a separation production module of the plant of FIG. 1.

The separaration module 4, shown in FIG. 4, comprises a tank 40 for the preparation of a buffer solution, provided with a stirrer and a fluid circulation jacket. To the tank 40 there are connected a salt inlet conduit 41, a water inlet conduit 42, conduits 43 and 44 for the inlet and outlet of cooling liquid from its jacket and a conduit 45 for the outlet of the buffer solution, provided with a volumetric pump 38. The outlet conduit 45 is connected to a respective inlet conduit 46 to each of two cooling tanks 47 and 48, to a conduit 49, in turn connected to an inlet conduit 66 in a centrifugal separator 50, to an inlet conduit 51 in an ultra-filtration unit 52 and to a conduit 53, in turn connected to an inlet conduit 67 in a homogenizing unit 54.

The ultra-filtration unit 52 can be present or not, in relation to the type of micro-organism treated. Similarly, the centrifugal separator 50 or the homogenizing unit 54 may also be missing. To the tank 47 there is connected a conduit 55 for the inlet of the fermented broth from the culture module 3, a conduit 56 for the inlet of the product from the homogenizing unit 54, conduits 57 and 58 for the inlet and outlet of the cooling fluid in its jacket, and a conduit 59 for the outlet of the product being processed, provided with a volumetric pump 38 and connected to the inlet conduit 66 in the centrifugal separator 50 and to the inlet conduit 51 in the ultra-filtration unit 52. To the tank 48 there are connected, in addition to the conduit 46, conduits 60, 61, 62, 63, 64 for the inlet of the product, from the centrifuge 50, from the ultra-filtration unit 52 and from the homogenizing unit 54. To the tank 48 there are also connected respective conduits 57 and 58 for the inlet and outlet of the cooling fluid from its jacket, and a conduit 65 for the outlet of the product being processed, provided with a volumetric pump 38, and in turn connected to the inlet conduit 67 in the homogenizing unit 54, to the conduit 68 connected to the inlet conduit 51 in the ultra-filtration unit 52, and to the outlet conduit 69 of the crude extracted product from the separation module 4.

Figure 5:
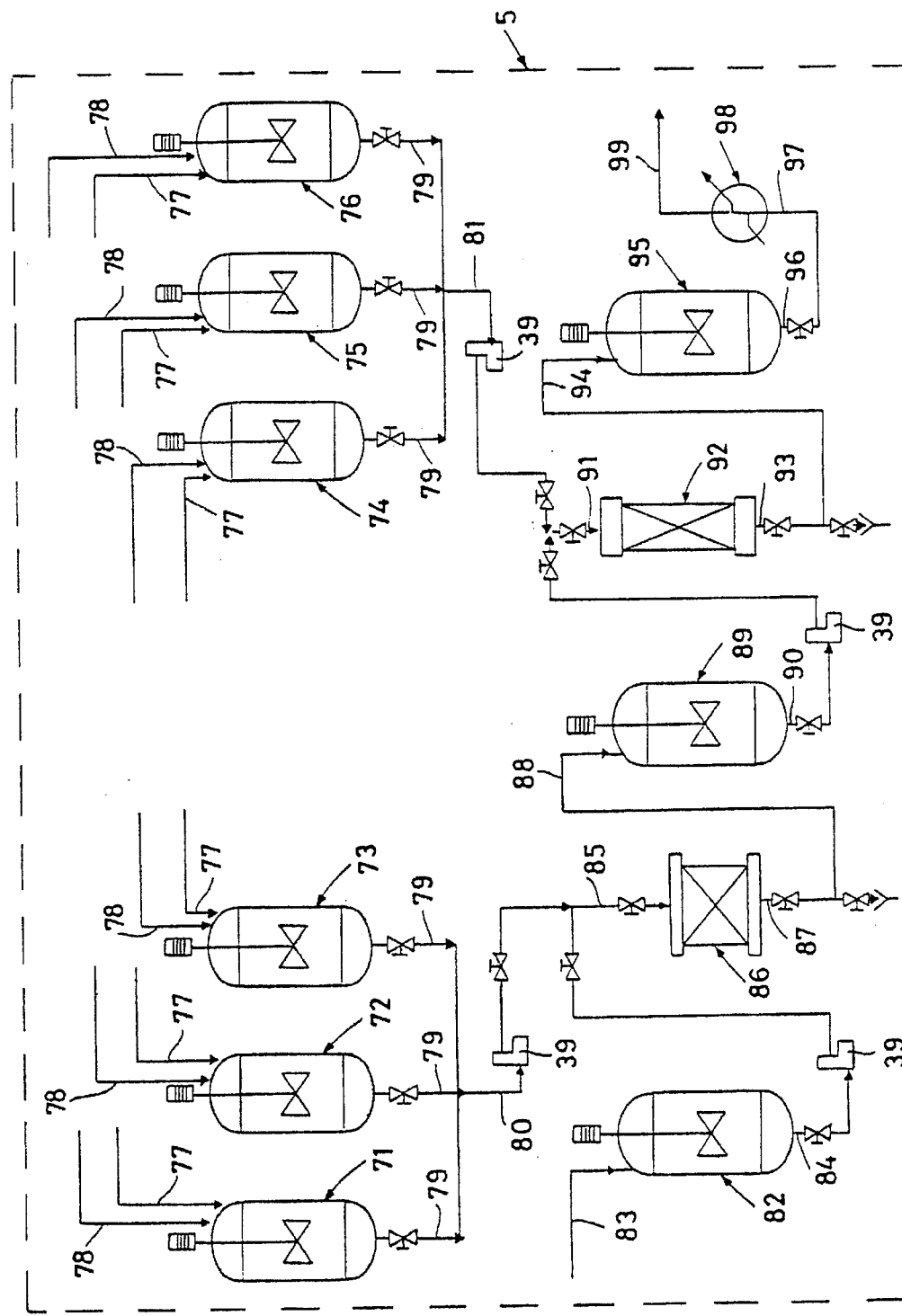
FIG. 5 shows schematically a purification and finishing production module of the plant of FIG. 1.

The purification and finishing module 5, as shown in FIG. 5, comprises tanks 71, 72, 73, 74, 75, 76 for the preparation of buffer solutions, provided with a stirrer; to every tank 71-76 there are connected a respective conduit 77 for the inlet of salts, a respective conduit 78 for the inlet of water for injection, and a respective conduit 79 for the outlet of the buffer solution; the outlet conduits 79 from the tanks 71, 72, 73 are connected to a collector conduit 80, provided with a volumetric pump 39, while the outlet conduits 79 from the tanks 74, 75, 76 are connected to a collector conduit 81, provided with a volumetric pump 39.

The purification and finishing module 5 comprises a tank 82 provided with a stirrer to which there is connected an inlet conduit 83 of the crude extracted product from the separation module 4; an outlet conduit 84, provided with a volumetric pump 39, is connected to an inlet conduit 85 in a first chromatography column 86 run by a computerized unit, not shown, to which the conduit 80 is also connected. An outlet conduit 87 from the chromatography column 86 is connected to an inlet conduit 88 in a tank 89 provided with a stirrer, an outlet conduit 90 of which, provided with a volumetric pump 39, is connected to an inlet conduit 91 in a second chromatography column 92 run by a computerized unit, not shown, to which the conduit 81 is also connected. An outlet conduit 93 from the chromatography column 92 is connected to an inlet conduit 94 in a tank 95 provided with a stirrer, an outlet conduit 96 of which is in turn connected in a discontinuous manner to the inlet 97 of a vacuum-freeze dryer 98, provided with an outlet 99.

The discontinuity of the loading of the vacuum-freeze dryer allows the possible re-use of the sequence of equipments located upstream in order to improve the product's purity.

Figure 6:
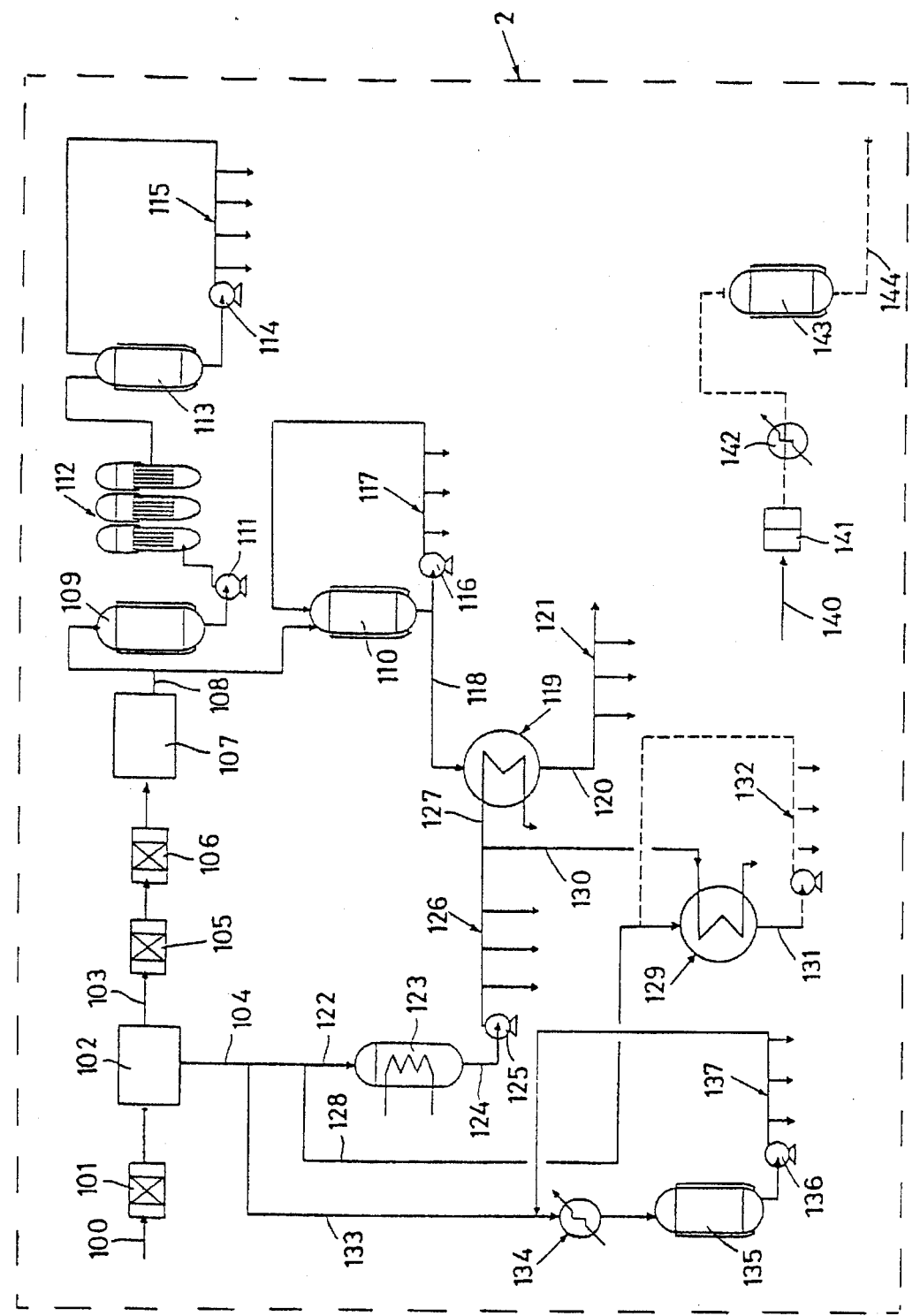
FIG. 6 shows schematically an auxiliary module of the plant of FIG. 1.

As shown in FIG. 6, the auxiliary service module 2 comprises a conduit 100 for feeding potable water, a sand filter 101 and a softener 102 provided with outlet conduits 103 and 104 of softened water. The auxiliary service module 2 comprises a 10-micron filter 105, an active-carbon filter 106 and a reverse osmosis unit 107 provided with an outlet conduit 108 for osmotized (purified) water connectd to tanks 109 and 110.

From the tank 109 the purified water is sent through a pump 111 to a multiple-effect distillation unit 112 producing water for injection (WFI) and discharges it into a storage tank 113, where it is kept at a given temperature, say 85° C.; a pump 114 sends the WFI to a circuit 115 connected to the modules 3, 4, 5; the circuit can also be of the non-recycling type.

From the tank 110 the purified water is sent, through a pump 116, to a circuit 117 connected to the modules 3, 4, 5; the circuit can also be of the non-recycling type. A conduit 118 supplies a clean-steam boiler 119 a clean-steam outlet conduit of which 120, for example at a maximum pressure of 3 bar, is connected to a circuit 121 in turn connected to the modules 3, 4, 5.

The outlet conduit 104 from the softener 102 feeds an inlet conduit 122 in an industrial-steam boiler 123, an outlet conduit of which 124 is connected, through a pump 125, to a circuit 126 for delivering industrial steam to the modules 3, 4, 5 and to an inlet conduit 127 in a heat exchanger of the clean-steam boiler 119.

The conduit 104 also supplies an inlet conduit 128 in a heat exchanger 129, that receives industrial steam from a conduit 130 and, by means of an outlet conduit 131 is connected to a circuit 132 for delivering hot water, e.g. at a temperature ranging from 50° C. to 70° C., to the modules 3, 4, 5. The conduit 104 further supplies an inlet conduit 133 in a cooling water production unit 134 that, by means of a tank 135 and a pump 136, is connected to a circuit 137 for delivering cooled water, say at a temperature of −5° C., to the modules 3, 4, 5.

The auxiliary module 2 also comprises an inlet conduit 140 for air, a compressor 141, a heath exchanger 142 and a storage tank 143, an outlet conduit 144 of which delivers compressed air to the modules 3, 4, 5.

The plant 1 according to the present invention can comprise just one of the production modules 3, 4, 5, or a combination of just two production modules, 3 and 4, or 3 and 5, or 4 and 5, possibly together with the auxiliary module 2, because each production module, enclosed in the corresponding container 6, forms a separate unit that may be used independently from, or in combination with, the others. Indeed, each production module or combinations of two production modules may be used together with plants already in existence that may need to be expanded or integrated with further treatment units, so as to meet widely-different needs.

An example of the utilization of the plant 1 illustrated as an example is constituted by the production of a hormone, through the controlled growth (fermentation) of a strain of a genetically-modified micro-organism. During growth this micro-organism produces a protein inside itself that, extracted from the cell (separation) and subsequently purified and vacuum-freezed dried (purification and finishing), shall constitute the final product.

The production process for obtaining the desired product starts with the operations of fermentation in the culture module 3, where multiplication of the micro-organism takes place through a series of successive steps.

The inoculum, grown in a flask in a microbiology laboratory, is introduced, through the conduit 29, in the 2-liter bioreactor 18 where the growth of the pre-vegetative takes place; this is transferred into the 20-liter bioreactor 19 where the growth of the vegetative takes place and this then passes into the 200-liter bioreactor 20 where it is performed the final fermentation, producing the fermented broth.

For the preparation of the fermentation culture media, maltose, meat extract, yeast extract are used as nutrients. These powder or liquid nutrient means contained in special metal containers arrive in the culture module 3, passing through the space for the passage of materials of an aseptic connecting module 8, wherein the external surface of the containers is cleaned by means of air jets and detergent solutions, so as to avoid the introduction inside the module of contaminants that could pollute the product. Each container holds a charge that is transferred directly, through the conduits 12, to each of the tanks 11 and 17, where the nutrient means are dissolved in water with an adequate degree of purity supplied by the conduits 13. All the tanks are then sterilized, with their content, at a given temperature, say 121° C., by sending into their jackets, through the conduits 14, industrial steam supplied by the circuit 126 of the auxiliary module 2.

The nutrients are loaded into the bioreactor 18 at the start of fermentation and then sterilized together with the bioreactor in an autoclave, not shown, after which, once the inoculum has been added, fermentation is started.

The delivery of the pre-vegetative to the bioreactor 19 and of the vegetative to the bioreactor 20 takes place through the pumps 27 and 35, while the nutrient means are supplied to the bioreactors 19 and 20 through the pumps 31 in successive portions, loading about 50% of the necessary quantity at the start of fermentation and the rest at a rate that is variable over time, e.g. from the sixth hour to the twelfth hour, when fermentation stops.

The fermented broth is transferred to the subsequent separation module 4 through the conduits 34 at outlet from the bioreactors 19 and 20, by pressurization with sterilized air; should it be necessary to cool it, it is recirculated in the tank 17 and transferred through the corresponding conduit 34 connected to the pump 31.

During fermentation, temperature is controlled through the delivery of cooled water supplied by the circuit 137 of the auxiliary module 2, to the jacket of each bioreactor 18, 19, 20 through the corresponding conduit 24, while the values of pH and foam are kept within the preset limits through the controlled additions of acid o base through the corresponding conduit 21 and of defoam agent through the corresponding conduit 32.

Air at inlet and outlet from the bioreactors 18, 19, 20, through the conduits 22 and 23, is sterilized through the corresponding filters.

Other raw materials, such as fermentation additives, or different materials, such as filters, enter the culture module 3 through the space for the passage of materials of the connecting module 8.

At the end of each fermentation cycle all equipments of the culture module 3 and the corresponding silicone pipings are washed and sterilized with a series of passages of basic and detergent solutions and water with an adequate degree of purity. The basic and detergent solutions are kept in wheeled containers, not shown, that are moved to the proximity of the place of usage and supplied by means of peristaltic pumps.

All materials at outlet from the culture module 3 are sterilized in an autoclave before they are taken outside. All wastes from washings, condensates, sealing fluids, emergency wastes, if any, at outlet from the bioreactors and from the tanks are collected in a single container and deactivated, through the direct injection of industrial steam, and cooled, by the addition of cool water, before being sent to a treatment tank that is outside the culture module 3.

Operations for the separation of the desired product take place in separation module 4.

After the fermentation cycles are over, the fermented broth is transferred to the tank 47 and then cooled to a given temperature, e.g. 4° C., through the delivery to its jacket, by means of the conduit 57, of cooled water, say at −5° C., supplied by the circuit 137 of the auxiliary module 2.

The subequent operation of concentration and washing of the biomass produced in the fermentation step takes place using the centrifugal separator 50 and, as a resuspension means, a buffer solution, say with TRIS (tri-hydroxide-methyl-amino-methane), supplied by the tank 40.

The product to be extracted from the micro-organism is an endogenous protein that is brought to a solution by breaking the micro-organism's cellular membrane. This operation is carried out by means of a certain number of passages through the homogenizing unit 54, after refrigerating in the tank 48, to whose jacket, through the conduit 57, cooling water from the circuit 137 of the auxiliary module 2 is supplied.

Once a satisfactory degree of breakage has been reached, the cellular fragments are eliminated from the suspension thus obtained by means of the centrifugal separator 50 already used for the separation of the biomass from the fermentation broth.

The clarified solution obtained is supplied to the purification module 5.

In this step, as before, all equipments and the corresponding silicone pipings, at the conclusion of their operating cycle, are washed and sterilized through the supply of basic and detergent solutions, as provided for in the case of the culture module 3.

Wastes from the separation module 4 are also sterilized by means of the direct injection of industrial steam and cobled before being sent to an external treatment tank.

In the purification module 5 the protein is purified in four steps, by means of which almost all the extraneous substances present are eliminated, until the product with the desired degree of purity is obtained.

All operations are carried out at a pre-set temperature, say 4° C. In the tank 82 the crude extract from the separation module 4 is stirred and cooled by means of the immersion of the tank itself in a container with ice or icy water. From the tank 82, the crude is sent to the first chromatography column 86 through the pump 39. The buffer solutions necessary for the different operations of elution, washing, regeneration and regeneration of the column 86 are prepared in tanks 71, 72, 73 and supplied by means of the pump 39. The sequence of addition and the quantity of each solution are controlled by the computer running the column 86.

The eluted fraction, containing the desired protein and some impurities, is collected in the tank 89, cooled and sent, through the pump 39, to the chromatography column 92. The desired fraction of the solution eluted from the column 92 is collected in the tank 95, sent back to the column 86, where it will be treated again with the operational sequences described above, at the end of which it shall be freeze dried in the vacuum-freeze dryer 98. At the end of the lyophilisation cycle, say after 24 hours, the desired product is collected and transferred to a special sterile container suitable for moving it outside.

All necessary raw materials, for example the powders for the preparation of the buffer solutions, gain access to the purification module 5 through the space for the passage of materials of a connection module 8 and all outgoing materials are sterilized in an autoclave before they are released, so as to avoid possible contaminations toward the outside.

Tanks 82, 89, 95 for supplying and discharging the product being processed and those 71–76 for supplying the buffer solutions and the corresponding silicone pipings are sterilised at the end of each operation through the operational sequences already described for modules 3 and 4.

Figure 7:
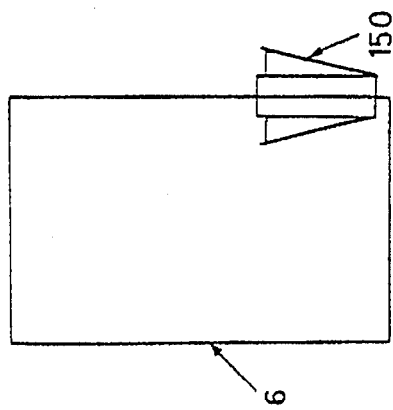
FIG. 7 shows schematically a device for the transfer of materials such as contaminated laboratory coats of the operators of the plant of FIG. 1.
Figure 8:
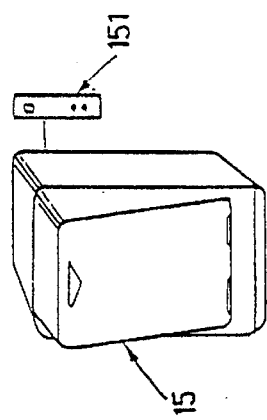
FIG. 8 shows on an enlarged scale the device of FIG. 7.

Modules 3, 4, 5 are also provided with an interlocking device for the transfer of contamined material, such as contamined operator laboratory coats, shown in FIGS. 7 and 8. The device comprises a basket 150 of suitable material, that can be opened both from the inside and from the outside of the container 6 of the corresponding module, but not simultaneously. A bag of material suitable for being sterilized, such a polyethylene, containing the contamined material, such as contamined laboratory coats, is positioned inside the basket 150, sterilized externally and then taken by an operator from the outside of the corresponding module. An interlocking control system, represented by the block 151, determines if the sterilization step is under way and enables the opening of the basket 150 either from the inside or from the outside of the corresponding module.

The plant 1 described as an example is in a position to meet the needs of different degrees of severity: class one, two and three.

A class-one plant is used to treat biological entities (such as micro-organisms, animal cells, vegetable cells), possibly genetically-modified, that have limited probabilities of causing diseases in man and that have limited survival and reproduction capabilities, without any negative consequences for the environment.

A class-two plant is used to treat biological entities (such as micro-organisms, animal cells, vegetable cells), possibly genetically-modified, that can cause diseases in man (for which preventive or therapeutic measures are in any case available) and constitute a risk for the operators, although it is not probable that they can propagate in the community. Such entitites may have significant involvement in environmental processes, interactions with other micro-organisms present in the environment and effects on them and capabilities of forming survival structures.

A class-three plant is used to treat biological entities (such as micro-organisms, animal cells, vegetable cells), possibly genetically-modified, that can cause serious diseases in man and constitute a serious risk for the operators. Such entities can propagate in the community, have significant involvement in environmental processes, interactions with other micro-organisms present in the environment and effects on them and capabilities of forming survival structures.

We claim:

1. A mobile-module plant for the development and the production on a pilot scale of a biotechnological product, said plant comprising
   (i) at least two mobile modules suitable for being connected together,
   (ii) each of said mobile modules comprising a movable container,
   (iii) one of said mobile modules being a development module which comprises a respective aseptic container wherein is housed at least one biological processing apparatus, and
   (iv) a second of said modules being a connecting module suitable to connect to one of said modules, said connecting modules comprising a respective aseptic container suitable to include a dressing room and to form a passage for the entry and exit of staff.

2. A plant according to claim 1, wherein said development module is a culture module and wherein the biological processing apparatus includes a nutrient formation tank and a bioreactor.

3. A plant according to claim 1, wherein said development module is a separation module and wherein the biological processing apparatus includes at least one of a buffer solution tank; a cooling tank; a centrifugal separator; a filter; and a homogenizing unit.

4. A plant according to claim 1, wherein said development module is a purification and finishing module and wherein the biological processing apparatus includes a buffer solution tank; at least one stirrer tank; at least one chromatography column; and, a vacuum freeze drier.

5. A plant according to claim 1, further comprising an auxiliary module comprising a movable container.

6. A plant according to claim 1, wherein said movable container is thermally insulated and is provided with a space for the passage of pipes for fluids and with a space suitable for housing an air conditioning system.

7. A plant according to claim 2, wherein at least one container of said modules is provided with a device for the transfer to the outside of a bag of material suitable for being sterilized, containing contaminated material, comprising a basket operationally connected to an interlocking control system to be operated and opened from the inside or from the outside of said container.

8. A plant according to claim 7, wherein said contaminated material includes contaminated operator laboratory coats.

9. A plant according to claim 1, further comprising a module for the culture of at least one biotechnological product, a module for the separation of at least one biotechnological product, a module for the purification and finishing of at least one biotechnological product, an auxiliary module and three connecting modules.

10. A plant according to claim 1, wherein the mobile modules are each mounted on a trailer suitable for being connected to a tractor.

11. A plant according to claim 1 wherein each of the mobile modules is suitable for being moved on a railway car.

12. A plant according to claim 5, wherein the auxiliary module comprises apparatus selected from a group consisting of an air conditioner; a water cooling unit; a steam boiler; a water softener; a reverse osmosis unit; a still; a heat exchanger; a hot water production system; and an air compressor.

* * * * *